US012661138B2

(12) United States Patent
Zhang

(10) Patent No.: US 12,661,138 B2
(45) Date of Patent: Jun. 23, 2026

(54) ARTICULATION MECHANISM FOR A SURGICAL DEVICE

(71) Applicant: Covidien LP, Mansfield, MA (US)

(72) Inventor: Jun Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 415 days.

(21) Appl. No.: 18/560,639

(22) PCT Filed: May 13, 2021

(86) PCT No.: PCT/CN2021/093580
§ 371 (c)(1),
(2) Date: Nov. 13, 2023

(87) PCT Pub. No.: WO2022/236770
PCT Pub. Date: Nov. 17, 2022

(65) Prior Publication Data
US 2024/0252193 A1      Aug. 1, 2024

(51) Int. Cl.
*A61B 17/29*          (2006.01)
(52) U.S. Cl.
CPC ...... *A61B 17/29* (2013.01); *A61B 2017/2927* (2013.01)
(58) Field of Classification Search
None
See application file for complete search history.

(56) References Cited

U.S. PATENT DOCUMENTS

| | | | | |
|---|---|---|---|---|
| 5,713,505 | A | * | 2/1998 | Huitema .......... A61B 17/07207 227/176.1 |
| 5,823,066 | A | | 10/1998 | Huitema et al. |
| 6,241,139 | B1 | | 6/2001 | Milliman et al. |
| 7,624,902 | B2 | * | 12/2009 | Marczyk .......... A61B 17/07207 227/176.1 |

(Continued)

FOREIGN PATENT DOCUMENTS

| | | |
|---|---|---|
| CN | 1903138 B | 1/2011 |
| CN | 1911183 B | 4/2011 |

(Continued)

OTHER PUBLICATIONS

Extended European Search Report for European Patent Application No. 21941342.4 mailed Dec. 11, 2024, 13 pages.

(Continued)

*Primary Examiner* — Carl H Layno
*Assistant Examiner* — Manolis Pahakis

(57) ABSTRACT

An articulation assembly for use with a surgical device includes a drive bar, a locking pin, a drive gear, and a yoke. The drive bar includes a base and a stem extending therefrom. The base includes first teeth. The locking pin engages the first teeth of the drive bar. The drive gear is operatively coupled to the drive bar. The drive gear includes second teeth defining a gap between adjacent second teeth. The gap is configured to receive a portion of the locking pin. The yoke is operatively coupled to the drive gear such that rotation of the drive gear causes axial displacement of the yoke. Rotation of the drive bar transitions the locking pin from a locked state to an unlocked state and rotates the drive gear when the locking pin is in the unlocked state such that the yoke is axially displaced.

20 Claims, 13 Drawing Sheets

(56)                 References Cited

U.S. PATENT DOCUMENTS

| | | | | | |
|---|---|---|---|---|---|
| 8,336,754 | B2 * | 12/2012 | Cappola | ........... | A61B 17/07207 227/19 |
| 8,353,437 | B2 * | 1/2013 | Boudreaux | .......... | A61B 17/295 227/176.1 |
| 8,979,827 | B2 * | 3/2015 | Cappola | ........... | A61B 17/07207 606/1 |
| 9,055,943 | B2 | 6/2015 | Zemlok et al. | | |
| 10,064,620 | B2 | 9/2018 | Gettinger et al. | | |
| 11,116,501 | B1 * | 9/2021 | Marecki | ............. | A61B 17/0686 |
| 2010/0264194 | A1 * | 10/2010 | Huang | ............. | A61B 17/07207 227/180.1 |
| 2012/0199629 | A1 | 8/2012 | Cappola et al. | | |
| 2014/0025046 | A1 * | 1/2014 | Williams | ......... | A61B 17/07207 606/1 |
| 2014/0048581 | A1 * | 2/2014 | Scirica | ............... | A61B 17/2909 606/1 |
| 2015/0320437 | A1 * | 11/2015 | Worrell | .......... | A61B 17/320068 606/169 |
| 2016/0302840 | A1 * | 10/2016 | Scheib | ........... | A61B 17/320092 |
| 2017/0086828 | A1 * | 3/2017 | Cappola | ........... | A61B 17/00234 |
| 2017/0175852 | A1 * | 6/2017 | Nicholas | ................... | F16H 1/22 |
| 2017/0281165 | A1 | 10/2017 | Harris et al. | | |

FOREIGN PATENT DOCUMENTS

| | | |
|---|---|---|
| CN | 101116631 B | 8/2011 |
| CN | 101011291 B | 2/2012 |
| WO | 2021/207143 A1 | 10/2021 |

OTHER PUBLICATIONS

International Search Report for Application No. PCT/CN2021/093580 dated Feb. 10, 2022, 8 pages.
Written Opinion for Application No. PCT/CN2021/093580 dated Feb. 10, 2022, 4 pages.

* cited by examiner

ARTICULATION MECHANISM FOR A SURGICAL DEVICE

FIELD

This disclosure is generally related to surgical devices for endoscopic use and, more particularly, to surgical devices including articulation mechanisms for articulating tool assemblies.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

During laparoscopic or endoscopic surgical procedures, access to a surgical site is achieved through a small incision or through a narrow cannula inserted through a small entrance wounds in a patient. Because of limited area available to access the surgical site, many endoscopic devices include mechanisms for articulating the tool assembly of the device about a pivot axis in relation to a body portion of the device.

A continuing need exists in the art for an articulating mechanism for a surgical device that can maintain a tool assembly in a constant or fixed position during firing of the stapling device in both non-articulated and articulated configurations of the tool assembly.

SUMMARY

In accordance with an aspect of the disclosure, an articulation assembly for use with a surgical device includes a drive bar, a locking pin, a drive gear, and a yoke. The drive bar includes a base and a stem extending therefrom. The base includes first teeth. The locking pin engages the first teeth of the drive bar. The drive gear is operatively coupled to the drive bar. The drive gear includes second teeth defining a gap between adjacent second teeth. The gap is configured to receive a portion of the locking pin. The yoke is operatively coupled to the drive gear such that rotation of the drive gear causes axial displacement of the yoke. Rotation of the drive bar transitions the locking pin from a locked state to an unlocked state and rotates the drive gear when the locking pin is in the unlocked state such that the yoke is axially displaced.

In an aspect, the drive gear may define a slot and the drive bar may include a boss slidable between opposing ends of the slot of the drive gear such that the drive bar imparts rotation to the drive gear when the boss engages one of the opposing ends of the slot of the drive gear.

In another aspect, the locking pin may include a spring biasing the locking pin towards the drive gear.

In yet another aspect, the locking pin may include a tapered portion configured to engage a lateral wall of the second teeth of the drive gear. The lateral wall may define a portion of the gap such that the tapered portion of the locking pin enables the locking pin to slide over the lateral wall of the second teeth to enable rotation of the drive gear.

In still yet another aspect, the articulation assembly may further include a knob coupled to the stem of the drive bar for concomitant rotation of therewith.

In still yet another aspect, the articulation assembly may further include a cover defining a bore to receive the stem of the drive bar therethrough. The cover may further include a stopper to limit rotation of the knob by a predetermined amount.

In an aspect, the articulation assembly may further include a drive pin coupling the drive gear to the yoke.

In another aspect, the drive pin may be coupled to the drive gear off-center.

In yet another aspect, the yoke may define a slot configured to receive the drive pin.

In still yet another aspect, the slot of the yoke may be orthogonal to a longitudinal axis defined by the yoke.

In still yet another aspect, the drive bar may define a slot dimensioned to receive the locking pin therethrough.

In still yet another aspect, the drive bar may include an inner surface that defines a portion of the slot of the drive bar and has the first teeth.

In an aspect, the slot of the drive bar may have a semi-circular profile.

In accordance with another aspect of the disclosure, a surgical instrument includes an elongate body including proximal and distal portions, an articulation assembly, a tool assembly supported on the distal portion of the elongate body, and an articulation rod. The articulation assembly includes a drive bar including a base and a stem extending from the base, a locking pin rotatably coupled to the base of the drive bar, a drive gear operatively coupled to the drive bar, and a yoke operatively coupled to the drive gear such that rotation of the drive gear causes axial displacement of the yoke. The drive gear includes teeth defining a gap between adjacent teeth. The gap is configured to receive a portion of the locking pin. The articulation rod interconnects the yoke and the tool assembly such that axial displacement of the yoke causes articulation of the tool assembly. Rotation of the drive bar transitions the locking pin from a locked state to an unlocked state and rotates the drive gear when the locking pin is in the unlocked state such that the yoke is axially displaced to articulate the tool assembly.

In an aspect, the drive gear may have a slot and the drive bar may include a boss slidable between opposing ends of the slot of the drive gear such that the drive bar imparts rotation to the drive gear when the boss engages one of the opposing ends of the slot of the drive gear.

In another aspect, the drive bar may define a slot and may include a side wall defining a portion of the slot of the drive bar. The side wall may include teeth configured to engage the locking pin.

In yet another aspect, the locking pin may include a spring biasing the locking pin towards the drive gear.

In still yet another aspect, the locking pin may include a tapered portion configured to engage a lateral wall of the teeth of the drive gear defining a portion of the gap such that the tapered portion enables the locking pin to slide over the lateral wall of the teeth of the drive gear to enable rotation of the drive gear.

In still yet another aspect, the articulation assembly may further include a pad interposed between the drive bar and the drive gear. The pad may have an annular configuration.

In still yet another aspect, the articulation assembly may further include a knob coupled to the stem of the drive bar for concomitant rotation of therewith.

BRIEF DESCRIPTION OF DRAWINGS

Various aspects of the disclosure are described herein below with reference to the drawings, wherein.

DETAILED DESCRIPTION

Figure 1:
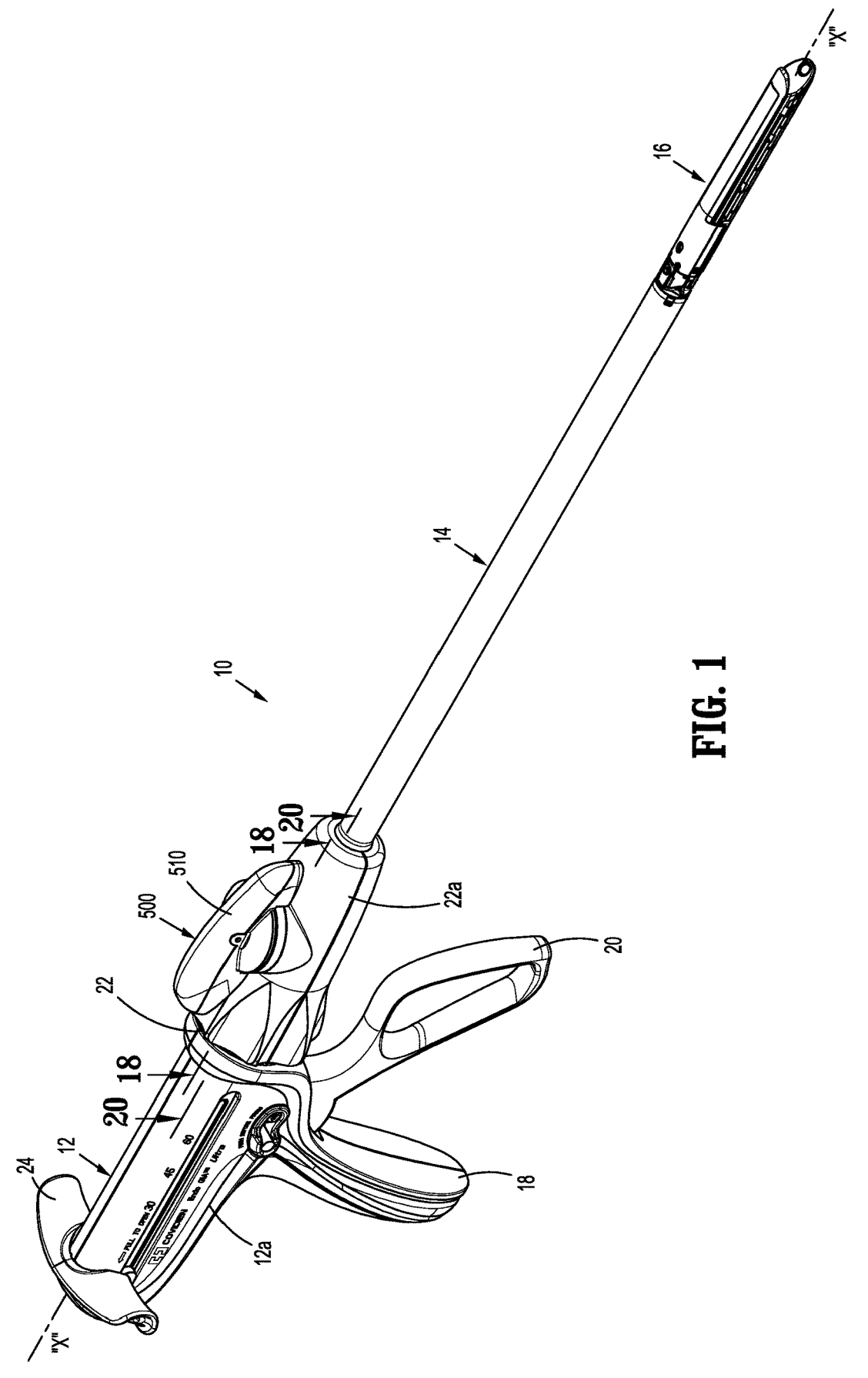
FIG. 1 is a perspective view of a surgical device in accordance with an aspect of the disclosure.

The disclosed surgical device including exemplary aspects of the disclosed articulation assembly will now be described in detail with reference to the drawings in which like reference numerals designate identical or corresponding elements in each of the several views. However, it is to be understood that the aspects of the disclosure included herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure. As used herein, the terms "parallel", "perpendicular", and "aligned" are understood to include relative configurations that are substantially parallel, substantially perpendicular, and substantially aligned, i.e., up to about + or −10 degrees from true parallel, true perpendicular, true alignment.

Figures 26, 27:
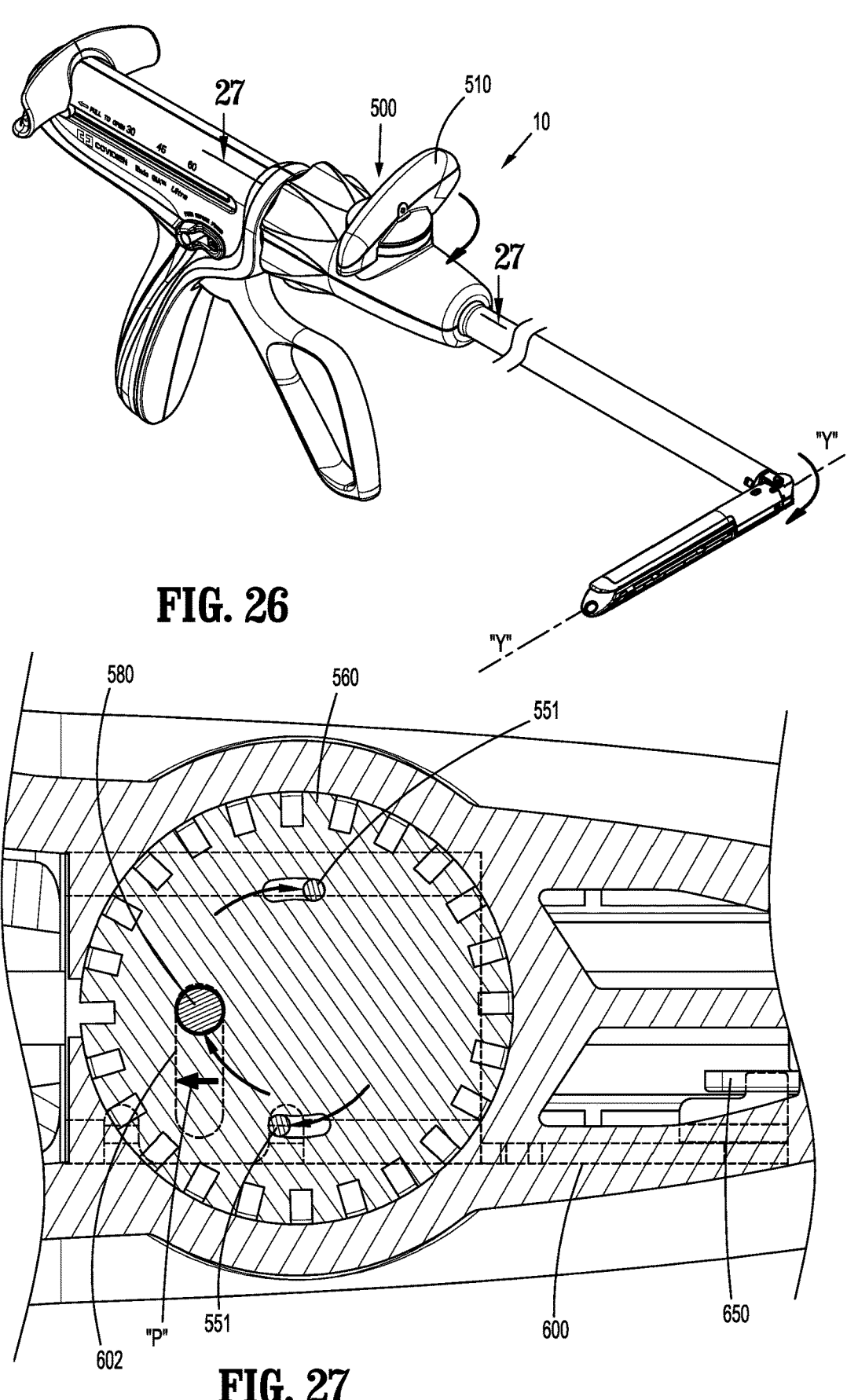
FIG. 26 is a perspective view of the surgical device of FIG. 1, illustrating articulation of a tool assembly of the surgical device.
FIG. 27 is a cross-sectional view of the surgical device of FIG. 26 taken along section line 27-27 of FIG. 26.

FIG. 1 illustrates a surgical device shown in the form of a stapling device 10 that includes a handle assembly 12, an elongate body or adapter 14, and a tool assembly 16. As illustrated, the handle assembly 12 is manually actuated and includes a stationary handgrip 18, a firing trigger 20, a rotation knob 22, and a retraction knob 24. The handle assembly 12 supports the elongate body 14 and includes a body 12a that defines the stationary handgrip 18. The firing trigger 20 is movable in relation to the stationary handgrip 18 to actuate various functions of the tool assembly 16 via the elongate body 14 including approximation, stapling, and cutting. The handle assembly 12 supports the rotation knob 22 that is engaged with the elongate body 14 such that rotation of the rotation knob 22 rotates the elongate body 14 and the tool assembly 16 in relation to the handle assembly 12 about a longitudinal axis "X-X" defined by the elongate body 14. A body 22a of the rotation knob 22 supports an articulation assembly 500 including an articulation lever 510 that is rotatable to articulate the tool assembly 16. The tool assembly 16 defines a longitudinal axis "Y-Y" (FIG. 26). The tool assembly 16 is pivotally coupled to the elongate body 14 and may pivot between a non-articulated configuration in which the longitudinal axes "X-X," "Y-Y" of the elongate body 14 and tool assembly 16 are aligned with each other and articulated configurations in which the longitudinal axes "X-X," "Y-Y" of the elongate body 14 and tool assembly 16 are offset from each other (FIG. 26).

Figure 2:
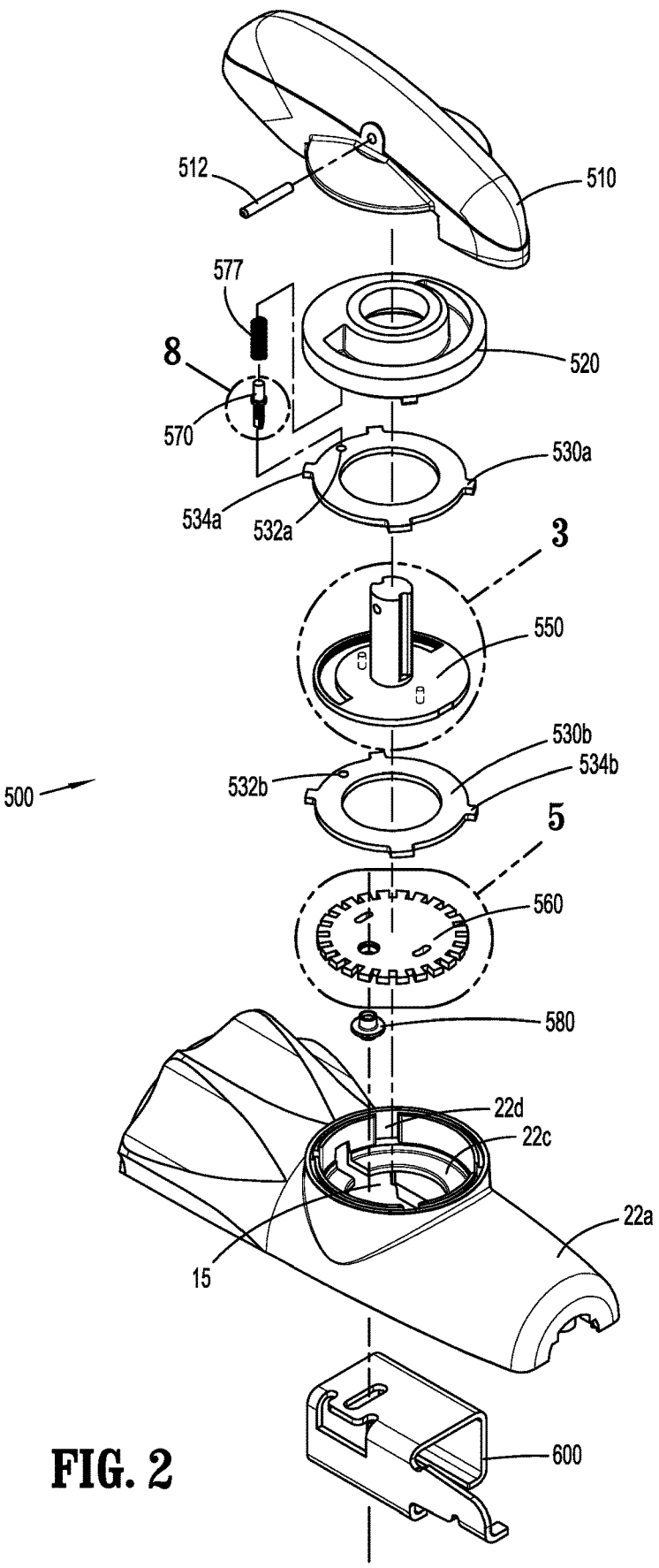
FIG. 2 is an exploded perspective view of an articulation assembly of the surgical device of FIG. 1.

FIG. 2 illustrates the articulation assembly 500 which is supported on the body 22a of the rotation knob 22. The articulation assembly 500 includes the articulation knob 510, a cover 520, first and second pads 530a, 530b, a drive bar 550, a drive gear 560, a locking pin 570, and a drive pin 580. The body 22a defines a cavity 15 and includes a lip 22c that extends radially inwards into the cavity 15 such that the drive gear 560 is rotatably supported on the lip 22c. The articulation assembly 500 is coupled to a yoke 600 that is slidably disposed within a cavity 15 of the body 22a. In particular, the yoke 600 is operatively coupled to the tool assembly 16 via an articulation rod 650 (FIG. 11) such that rotation of the articulation knob 510 causes longitudinal translation of the in articulation rod 650 to transition the tool assembly 16 between the articulated and non-articulated configurations.

Figure 3:
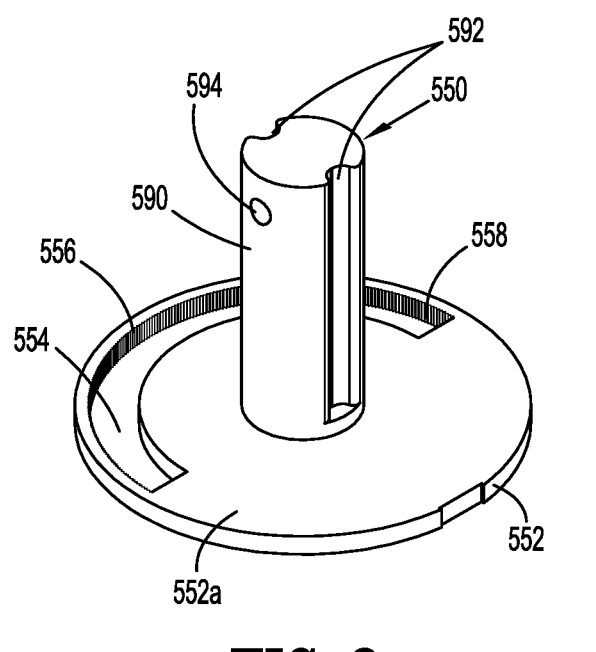
FIG. 3 is an enlarged view of the indicated area of detail of FIG. 2.
Figure 4:
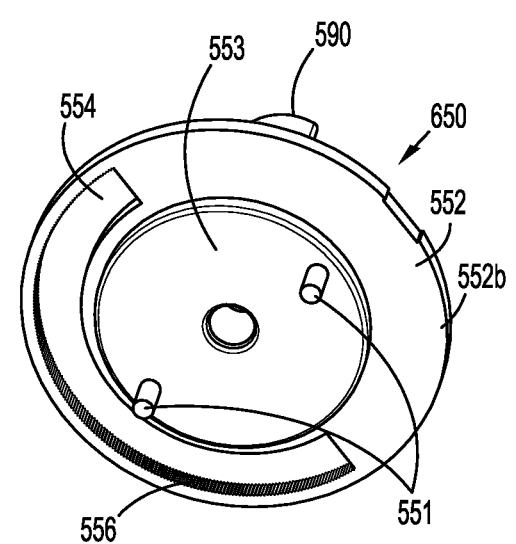
FIG. 4 is a bottom perspective view of a drive bar of FIG. 3.

FIGS. 3 and 4 illustrate the drive bar 550 that is configured to impart rotation of the articulation knob 510 (FIG. 2) to the drive gear 560 (FIG. 2). The drive bar 550 includes a base 552 having a circular profile, and a stem 590 extending from the base 552. The base 552 defines a slot 554 that may be, e.g., semi-circular. However, it is contemplated that the slot may have other profiles depending on, e.g., a terminal, articulation angle. The base 552 includes a side wall 556 that defines a portion of the slot 554 and includes teeth 558 configured to engage the locking pin 570, as will be described. The base 552 further includes opposing first and second surfaces 552a, 552b. The first pad 530a (FIG. 2) is in a superposed relation with the first surface 552a, and the second surface 552b is in a superposed relation with the second pad 530b (FIG. 2). In particular, the second surface 552b include a platform 553 that is, e.g., concentrically, disposed with respect to the base 552 such that at least a portion of the platform 553 is positioned radially inwards of the slot 554. The platform 553 includes bosses 551 that are configured to operatively engage the drive gear 560 (FIG. 2), as will be described below. In aspects of the disclosure, the bosses 551 may diametrically oppose each other. The stem 590 extends away from the first surface 552a. In particular, the stem 590 defines grooves 592 along a length of the stem 590 to receive complementary radial protrusions 511 (FIG. 7) of the articulation knob 510 in order to inhibit relative rotational movement between the stem 590 and the articulation knob 510. In an aspect, the grooves 592 may diametrically oppose each other. In addition, the stem 590 of the drive bar 550 defines a bore 594 that is orthogonal to the length of the stem 590. The bore 594 is dimensioned to receive a pin 512 (FIG. 2) to secure the drive bar 550 with the articulation knob 510 (FIG. 2) for concomitant rotation therewith.

As described above, the first and second pads 530a, 530b (FIG. 2) are disposed on opposing first and second surfaces 552a, 552b of the base 552 of the drive bar 550. The first and second pads 530a, 530b are substantially identical to each other and have an annular configuration. The first and second pads 530a, 530b each include circumferentially arranged tabs 534a, 534b that are received in recessed portions 22d (FIG. 2) of the body 22a of the rotation knob 22 to inhibit rotation of the first and second pads 530a, 530b relative to the elongate body 14.

Figure 5:
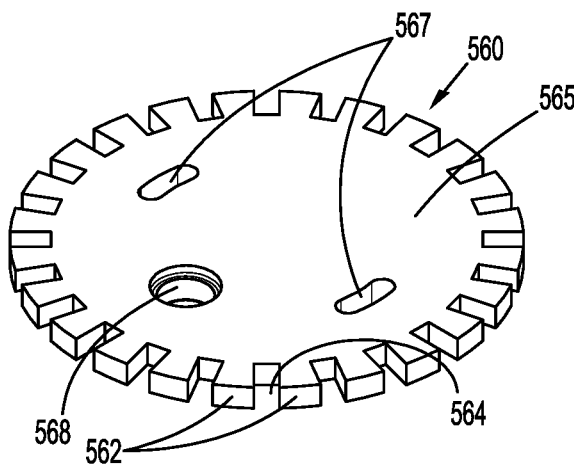
FIG. 5 is an enlarged view of the indicated area of detail of FIG. 2.
Figure 6:
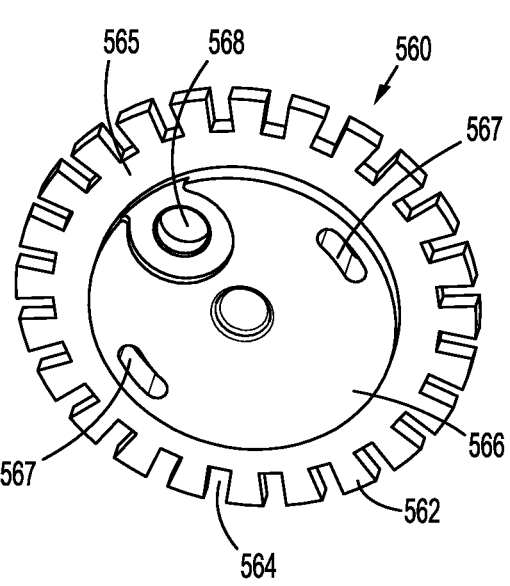
FIG. 6 is a bottom perspective view of a drive gear of FIG. 5.

FIGS. 5 and 6 illustrate the drive gear 560 which includes a base 565 and an engaging portion 566 concentrically disposed on the base 565. A portion of the base 565 is disposed on the lip 22c (FIG. 2) of the body 22a of the rotation knob 22. The engaging portion 566 is dimensioned to be rotatably supported radially within the lip 22c. The base 565 has a plurality of teeth 562. Adjacent teeth 562 define a gap 564 therebetween. The plurality of teeth 562 may be in registration with the lip 22c. The drive gear 560 defines a bore 568 configured to receive a drive pin 580 (FIG. 2) that couples the drive gear 560 to the yoke 600 (FIG. 2), and slots 576 that diametrically oppose each other. Each slot 576 is configured to receive a corresponding boss 551 (FIG. 4) of the drive bar 550. Each slot 576 is dimensioned to enable movement of a respective one of the bosses 551 between opposite ends of the corresponding slot 576, as will be described below.

Figures 7, 8, 9:
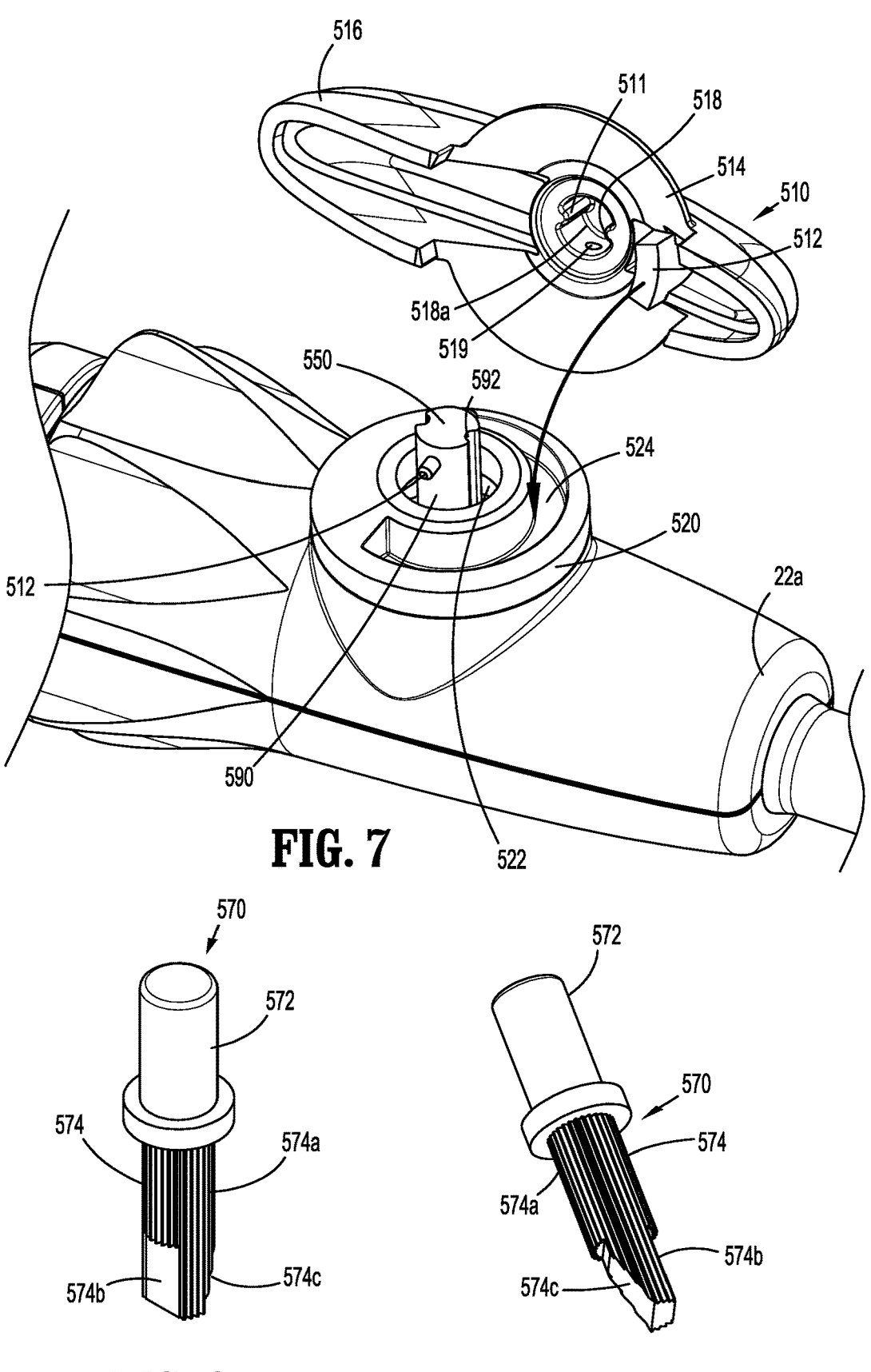
FIG. 7 is a perspective view of a body of a rotation knob of FIG. 2, illustrating an articulation knob separated from the articulation assembly supported on the body of the rotation knob.
FIG. 8 is an enlarged view of the indicated area of detail of FIG. 2.
FIG. 9 is a rear perspective view of a locking pin of FIG. 8.

FIG. 7 illustrates the drive bar 500 mounted on the lip 22c (FIG. 2) of the body 22a of the rotation knob 22. The articulation knob 510 is rotatably securable to the cover 520. In particular, the articulation knob 510 includes a circular base 514 in registration with the cover 520, and a knob portion 516 formed as a single construct with the circular base 514 for concomitant rotation. The circular base 514 includes a tab 512 extending towards the cover 520. The articulation knob 510 includes an engaging portion 518 defining a recess 518a configured to receive a portion of the stem 590 of the drive bar 550. In an aspect, the engaging portion 518 of the articulation knob 510 may include radial protrusions 511 configured to be received in the grooves 592 of the stem 590 of the drive bar 550 to inhibit relative rotation between the articulation knob 510 and the drive bar 550. In an aspect, the radial protrusions 511 may diametrically oppose each other. The articulation knob 510 may be coupled to the stem 590 of the drive bar 550 through a use of the pin 512. In an aspect, the articulation knob 510 may define a transverse bore 519 to receive the pin 512 transversely extending through the stem 590. However, other methods of coupling the drive bar 550 to the articulation knob 510 are envisioned such as, e.g., ultrasonic welding, adhesion, snap-fitting, or friction-fitting, etc. may be utilized.

The cover 520 defines a bore 522 configured to receive the stem 590 of the drive bar 550 therethrough, and a circumferential groove 524 having, e.g., a semi-circular, profile. The circumferential groove 524 is configured to receive the tab 512 of the articulation knob 510 to facilitate a predetermined amount of rotation of the articulation knob 510 in relation to the cover 520. For example, the circumferential groove 524 having the semi-circular profile, as shown, enables rotation of the articulation knob 510 of about 180 degrees.

Figures 12, 13:
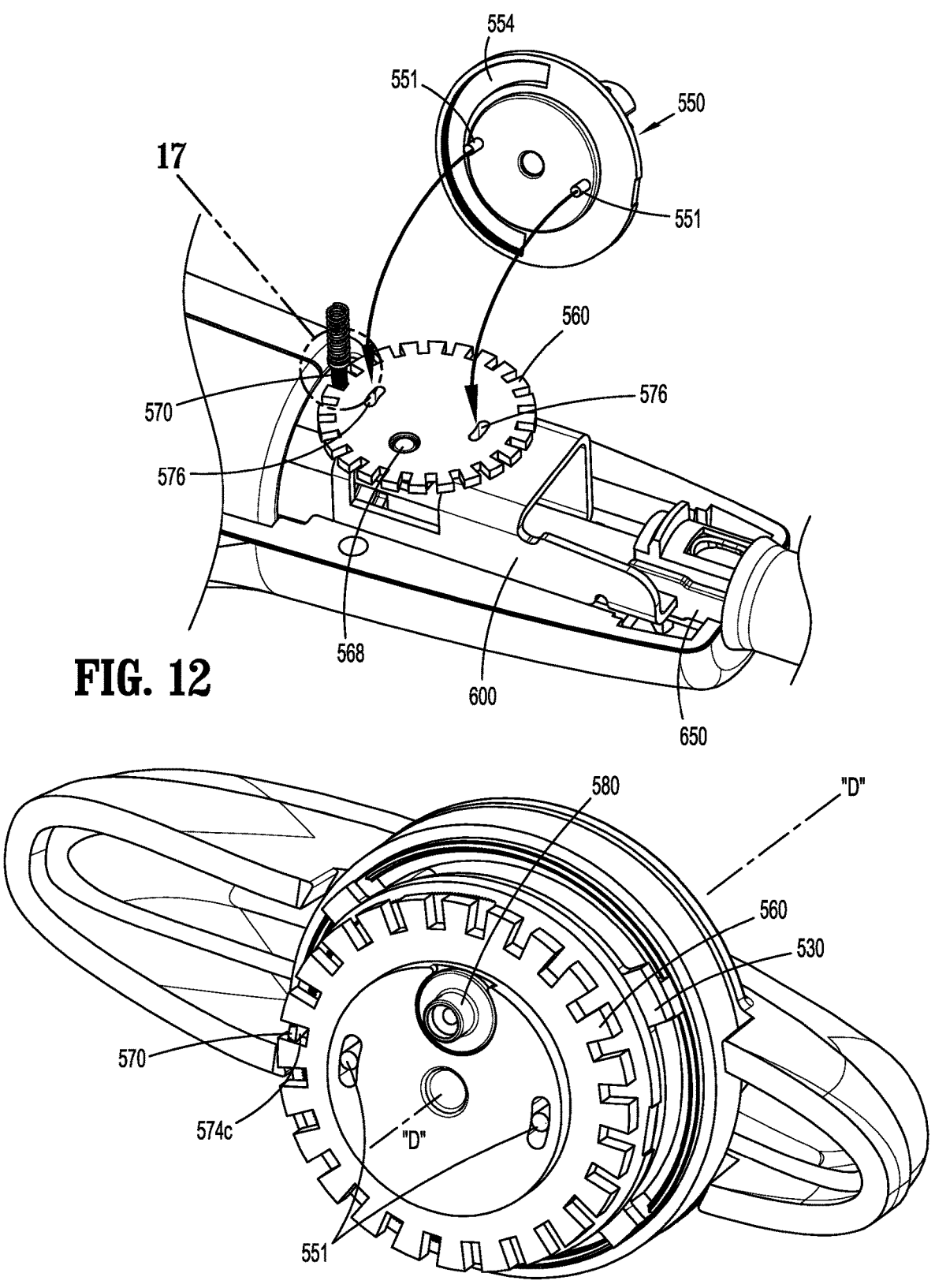
FIG. 12 is a partial perspective view of the body of the rotation knob of FIG. 11, illustrating coupling of a drive bar of the articulation assembly to the drive gear of the articulation assembly.
FIG. 13 is a bottom perspective view of the articulation assembly of FIG. 1.

FIGS. 12 and 13 illustrate coupling of the drive bar 550 to the drive gear 560. Each boss 551 of the drive bar 550 is received in one of the corresponding slots 576 of the drive gear 560. In particular, each slot 576 is larger than the corresponding boss 551 to enable movement of the corresponding boss 551 therein. Each boss 551 is movable between opposing ends of the corresponding slot 576. The drive bar 550 imparts rotation to the drive gear 560 when the bosses 551 engage the ends of the slots 576. In an aspect, the slots 576 may diametrically oppose each other and may also have the same radius of curvature.

Figure 14:
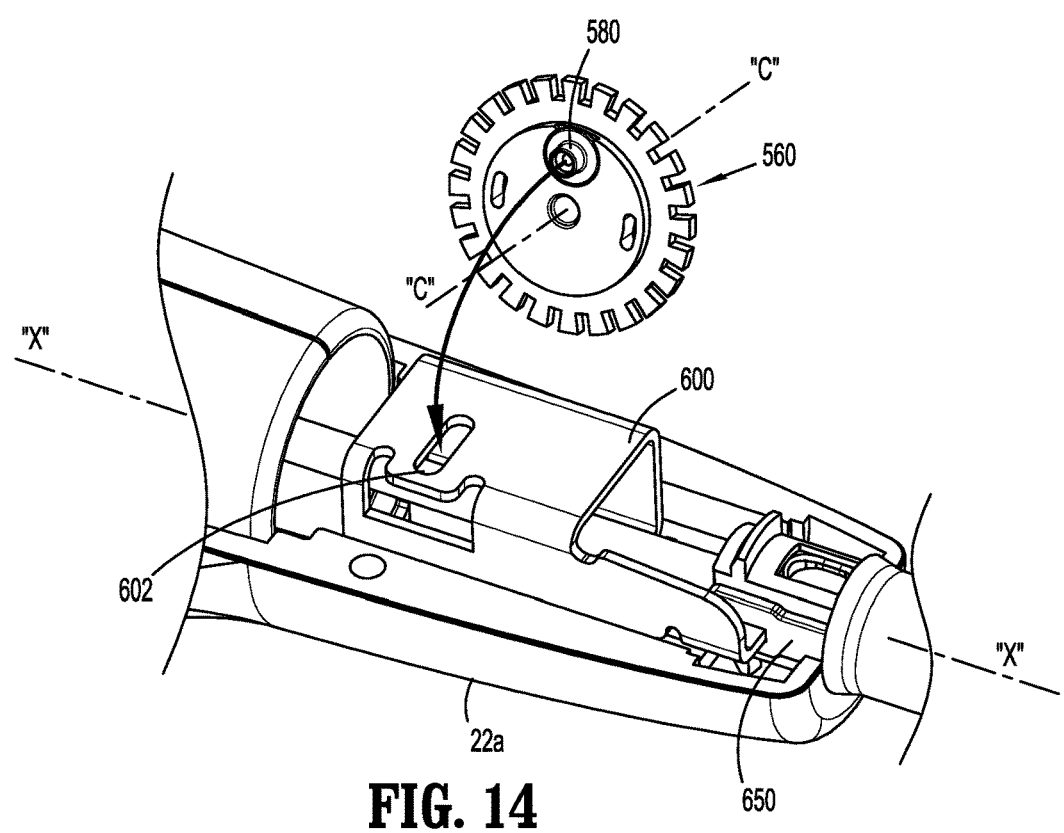
FIG. 14 is a partial perspective view of the body of the rotation knob, illustrating coupling of the drive gear of the articulation assembly to the yoke.

FIG. 14 illustrates coupling of the drive gear 560 to the yoke 600 via the drive pin 580. The drive pin 580 is secured to the bore 568 (FIG. 5) of the drive gear 560. The drive pin 580 is positioned off-center of the drive gear 560 and is slidably received in a slot 602 defined in the yoke 600. The slot 602 may be transverse to the longitudinal axis "X-X" of the elongate body 14. The yoke 600 is slidably received in the body 22a of the rotation knob 22. Under such a configuration, rotation of the drive gear 560 causes axial displacement of the yoke 600. The yoke 600 is coupled to the articulation rod 650 to impart axial displacement to the articulation rod 650 that is operatively coupled to the tool assembly 16 (FIG. 1) to effect articulation of the tool assembly 16.

Figure 10:
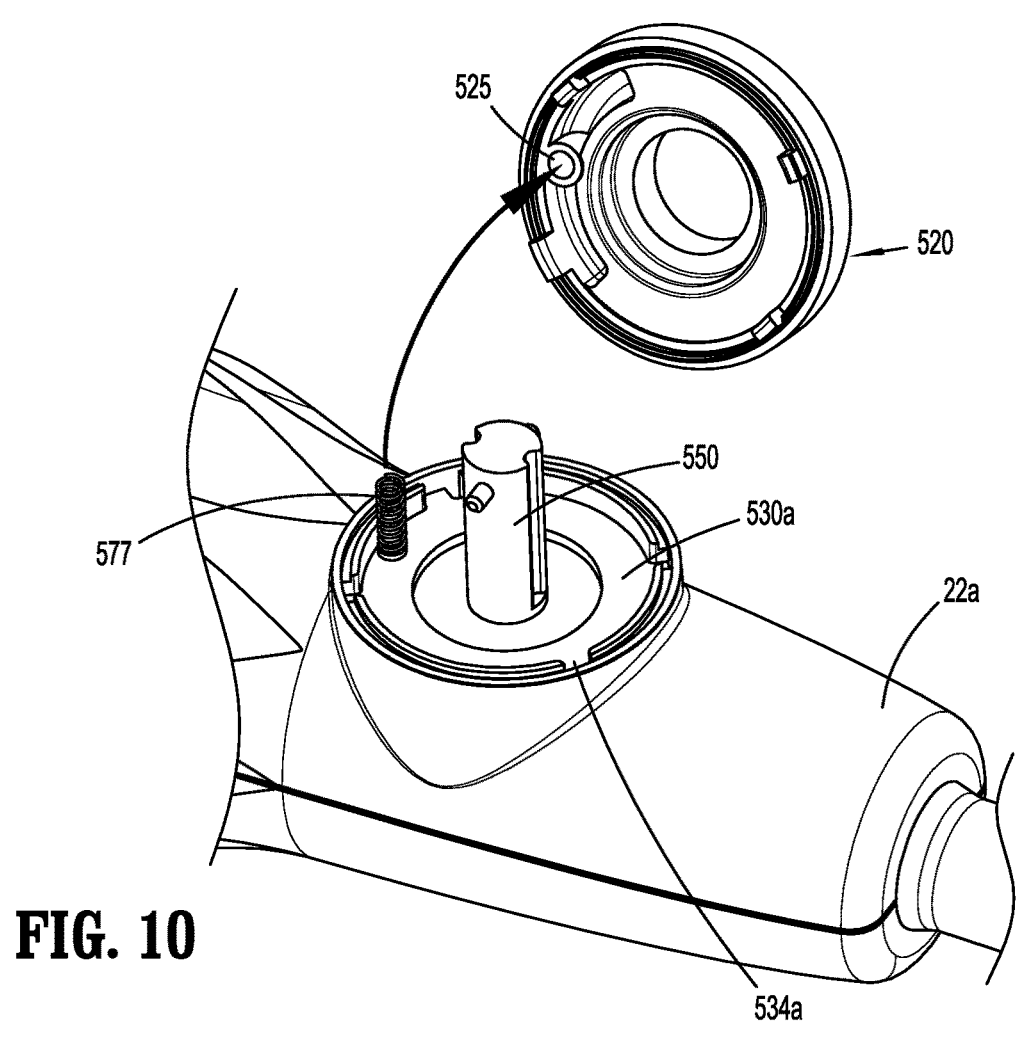
FIG. 10 is a perspective view of the body of the rotation knob of FIG. 7, illustrating a cover separated from the articulation assembly supported on the body of the rotation knob.
Figure 11:
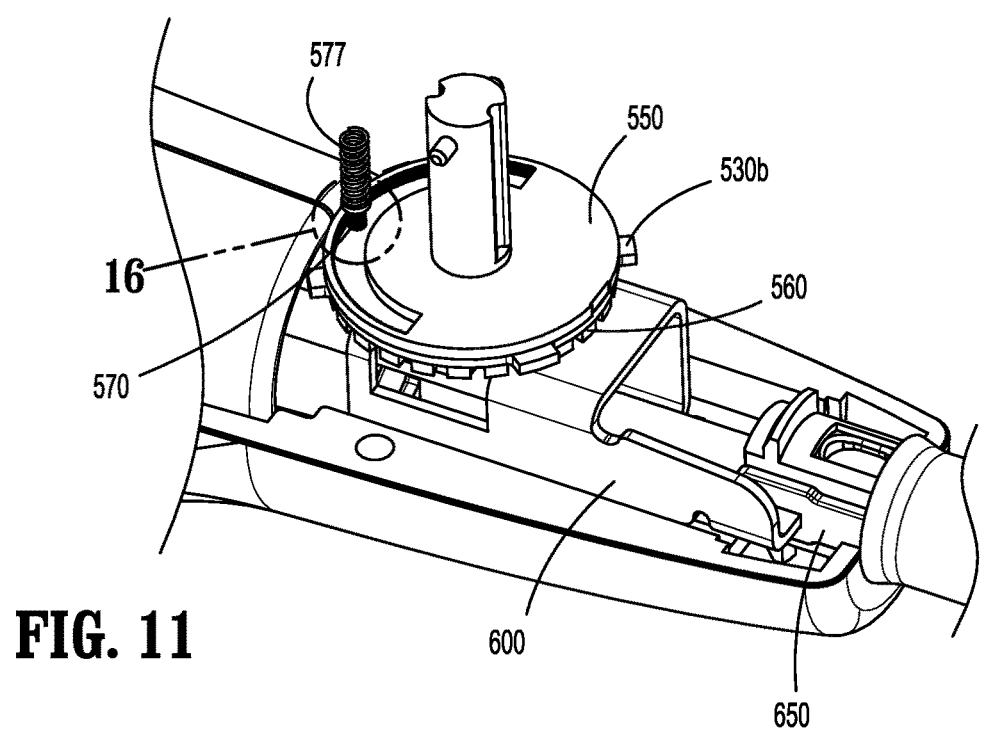
FIG. 11 is a partial perspective view of the body of the rotation knob of FIG. 10 with a portion of the body removed.
Figure 15:
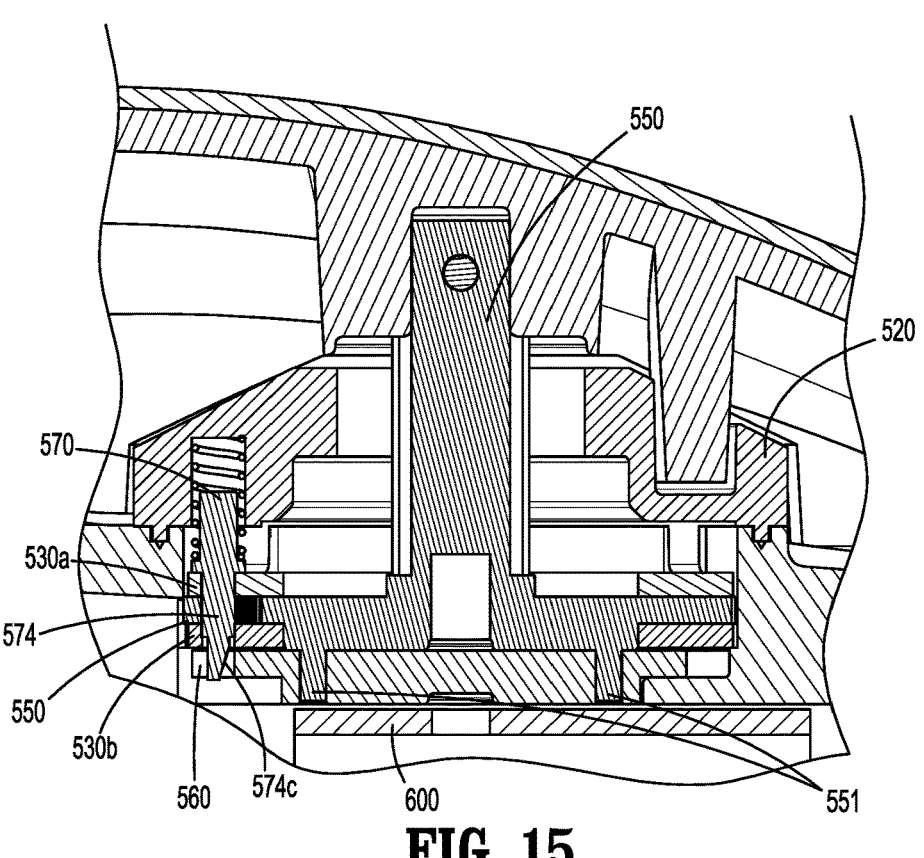
FIG. 15 is a partial side cross-sectional view of the body of the rotation knob of FIG. 1, illustrating the articulation assembly.

FIGS. 8 and 9 illustrate the locking pin 570 that is configured to selectively inhibit rotation of the drive gear 560 (FIG. 5), which, in turn, inhibits articulation of the tool assembly 16 (FIG. 1) or maintains the articulated or non-articulation configuration of the tool assembly 16. The locking pin 570 includes a head portion 572 that supports a spring 577 (FIG. 2) and an engaging portion 574 that includes teeth 574a. As shown in FIGS. 10 and 11, the head portion 572 of the locking pin 570 is rotatably secured in a hole 525 defined in the cover 520. As shown in FIG. 15, the engaging portion 574 extends through bores 532a, 532b (FIG. 2) of the first and second pads 530a, 530b and the slot 554 (FIG. 3) of the drive bar 550 and is received in one of the gaps 564 (FIG. 5) defined between adjacent teeth 562 of the drive gear 560. The first and second pads 530a, 530b support the locking pin 570 and further provide smooth axial displacement of the locking pin 570. In this manner, the teeth 574*a* (FIG. 8) of the engaging portion 574 of the locking pin 570 engage the teeth 558 (FIG. 3) of the drive bar 550, and the flat and tapered portions 574*b*, 574*c* of the locking pin 570 are disposed in one of the gaps 564 of the drive gear 560. Under such a configuration, the locking pin 570 may rotate upon rotation of the articulation knob 510 (FIG. 2), which, in turn, changes the orientation of the flat and tapered portions 574*b*, 574*c* of the locking pin 570 relative to the gap 564 of the drive gear 560, as will be described below.

Figure 16:
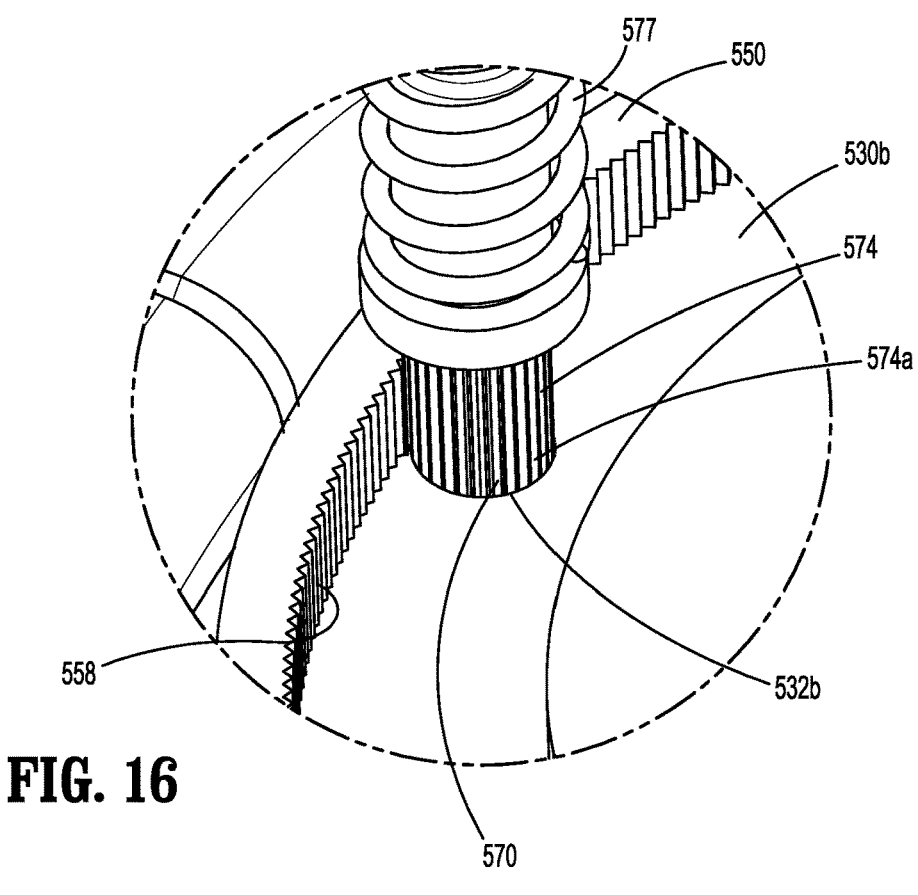
FIG. 16 is an enlarged view of the indicated area of detail of FIG. 11.
Figure 17:
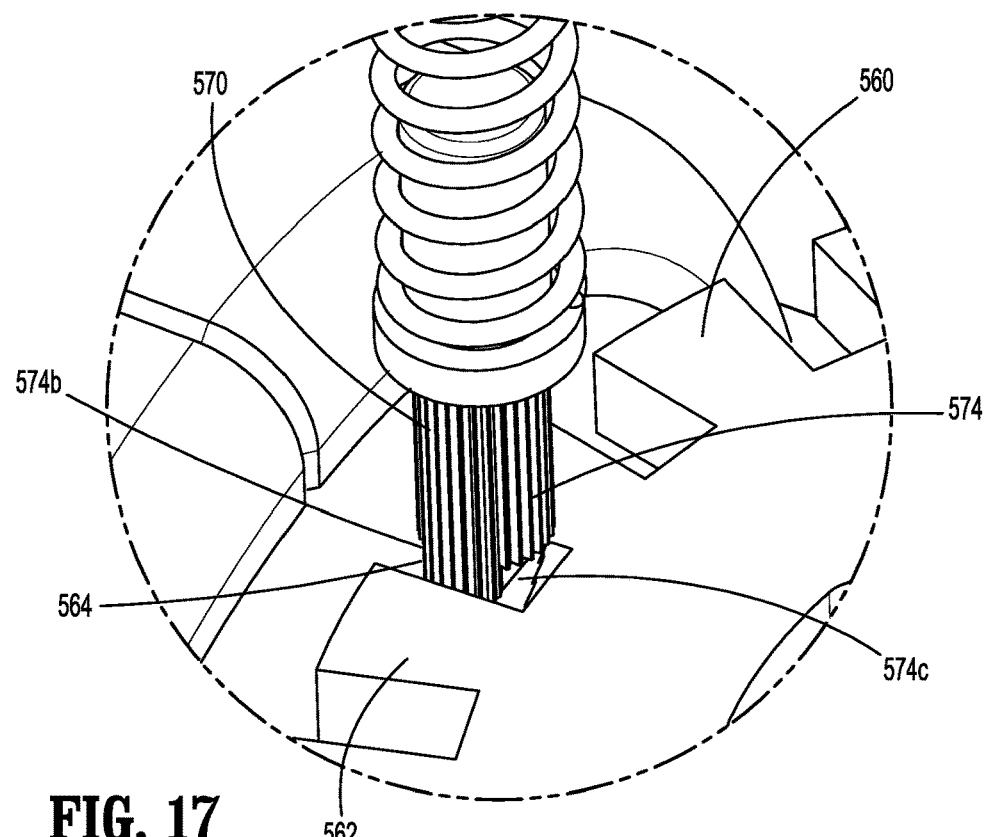
FIG. 17 is an enlarged view of the indicated area of detail of FIG. 12.
Figure 18:
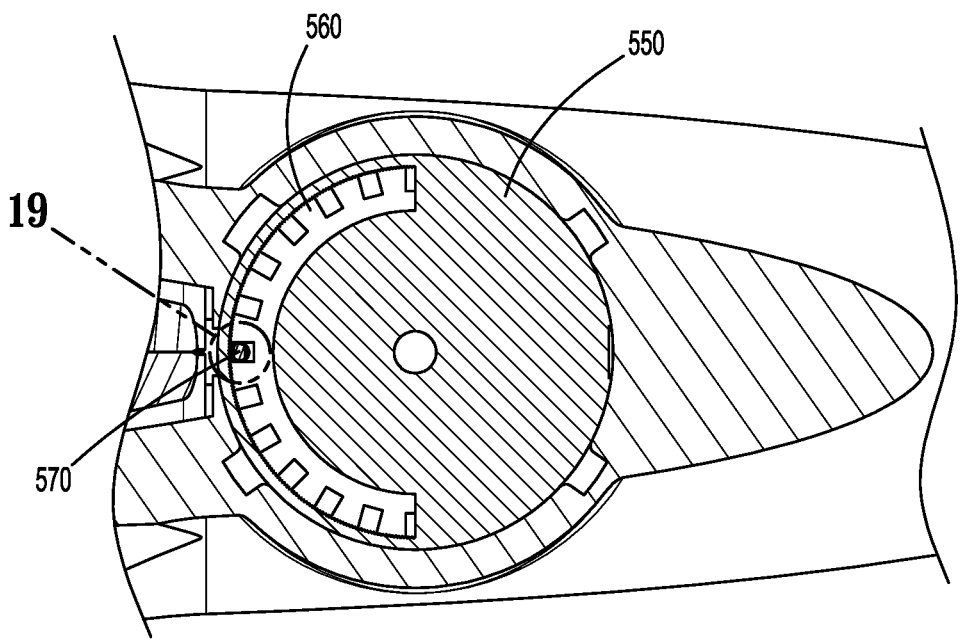
FIG. 18 is a cross-sectional view of the body of the rotation knob taken along section line 18-18 of FIG. 1.
Figure 19:
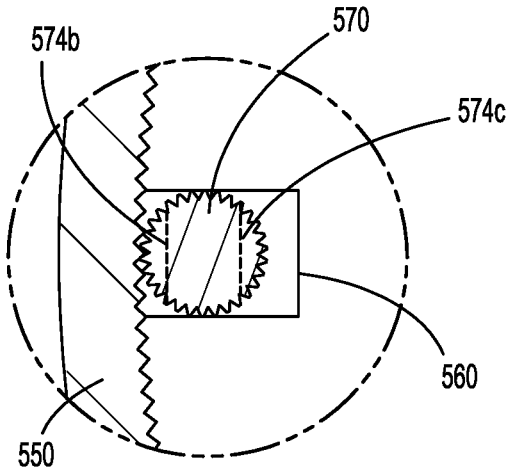
FIG. 19 is an enlarged view of the indicated area of detail of FIG. 18.
Figure 20:
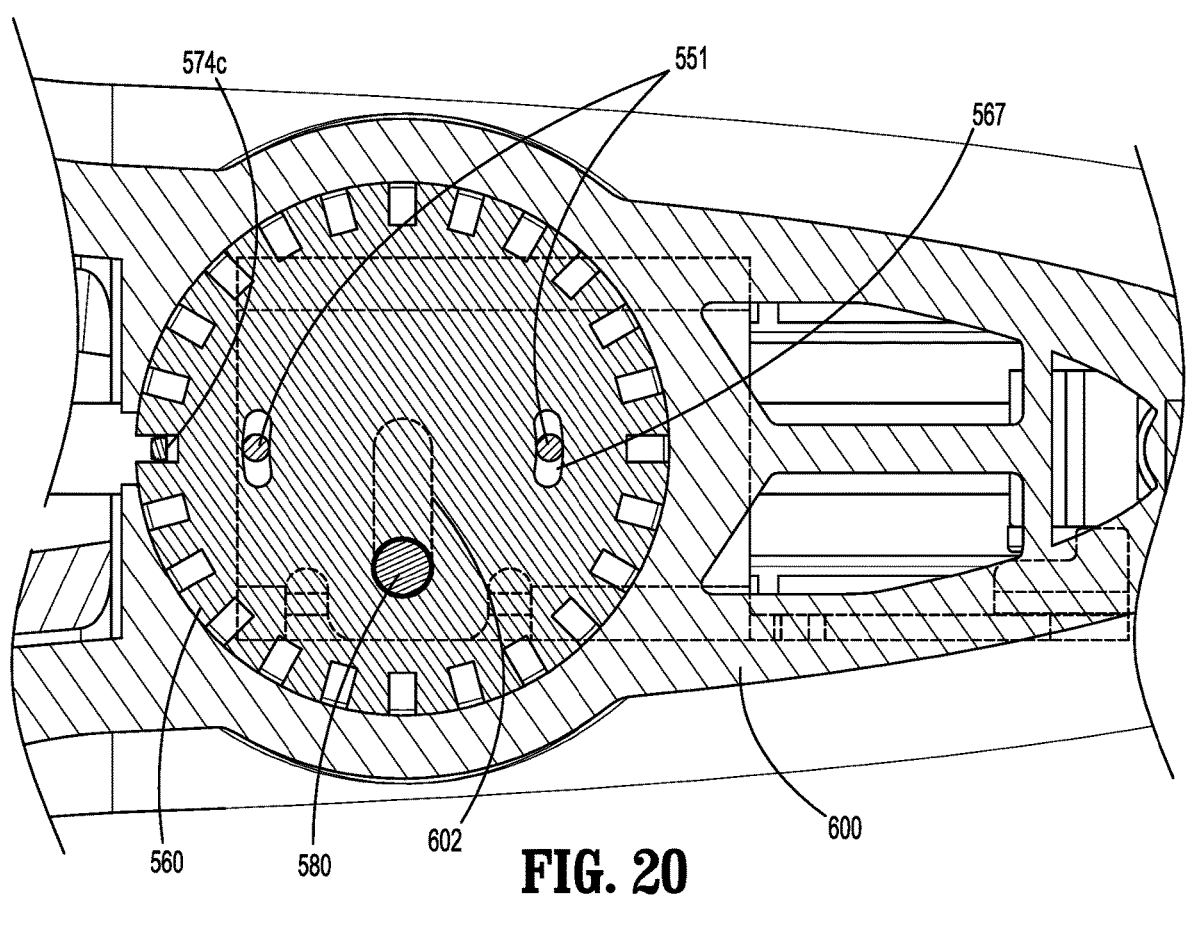
FIG. 20 is a cross-sectional view of the body of the rotation knob taken along section line 20-20 of FIG. 1.
Figure 21:
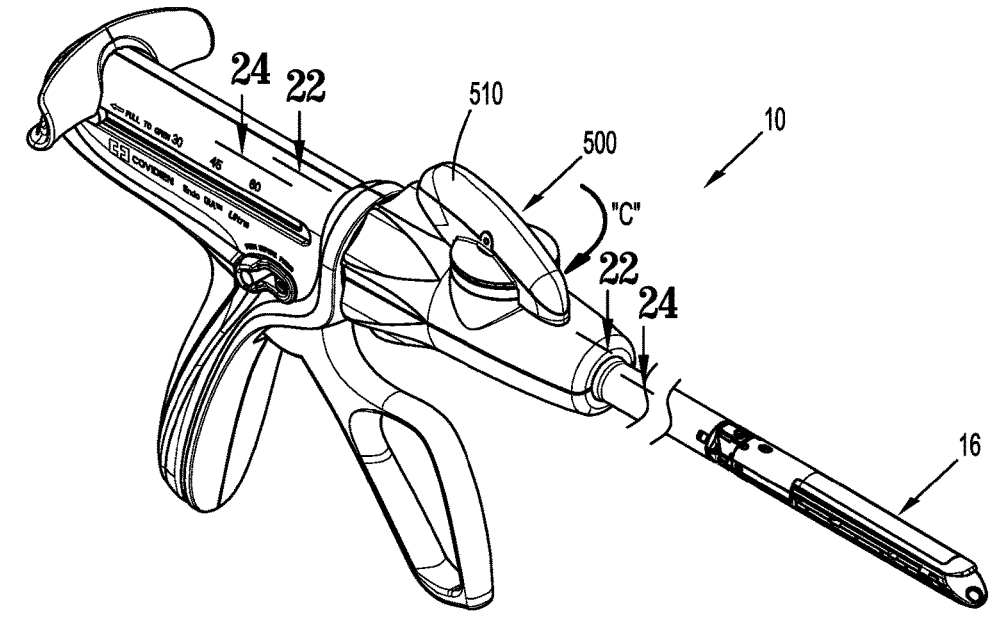
FIG. 21 is a perspective view of the surgical device of FIG. 1, illustrating rotation of the articulation knob of the articulation assembly.
Figure 22:
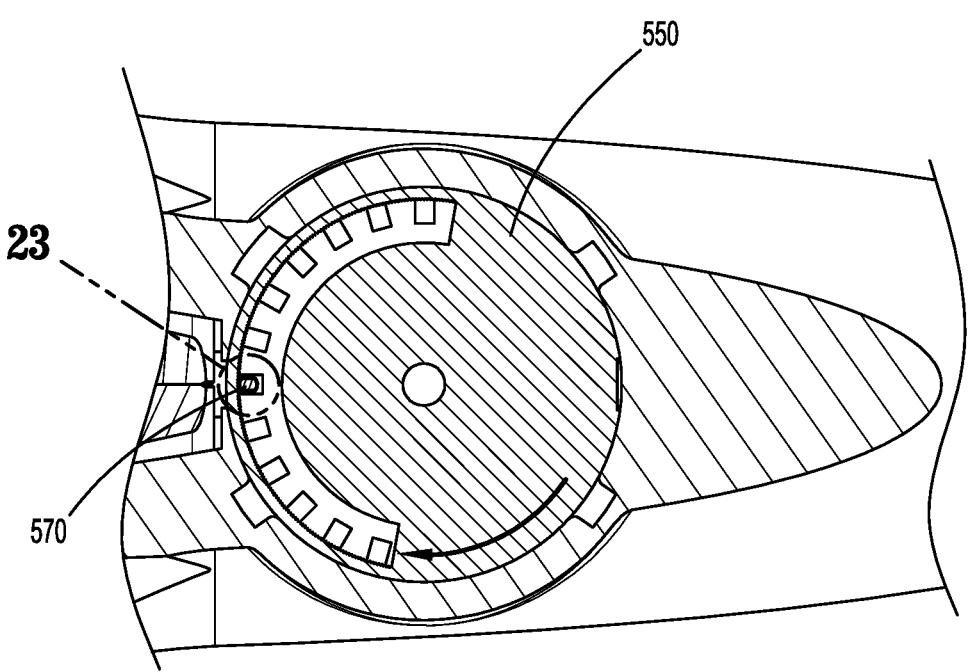
FIG. 22 is a cross-sectional view of the body of the rotation knob of FIG. 21 taken along section line 22-22 of FIG. 21.

FIGS. 15-17 illustrate the locking pin 570 operatively engaging the drive bar 550 and the drive gear 560. The teeth 574*a* of the engaging portion 574 of the locking pin 570 engage the teeth 558 of the drive bar 550 such that rotation of the articulation knob 510 rotates the locking pin 570. The locking pin 570 further extends through the bore 532*b* of the second pad 530*b* and is disposed within a gap 564 defined between adjacent teeth 562 of the drive gear 560. As shown in FIGS. 18 and 19, when the tool assembly 16 is in the unarticulated configuration (FIG. 1), the flat portion 574*b* of the locking pin 570 faces radially outwards of the tapered portion 574*c*. As shown in FIG. 20, under such a configuration, the bosses 551 of the drive bar 550 are centered in the slots 567 of the drive gear 560, and a drive pin 580 is positioned in one of the opposing ends of the slot 602 of the yoke 600.

Figure 23:
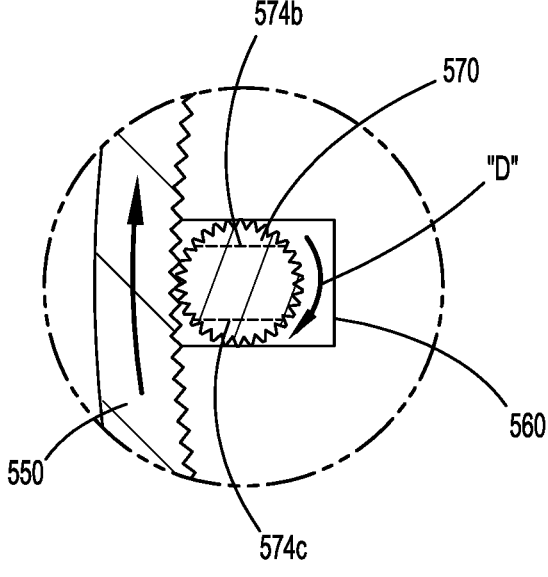
FIG. 23 is an enlarged view of the indicated area of detail of FIG. 22.
Figure 24:
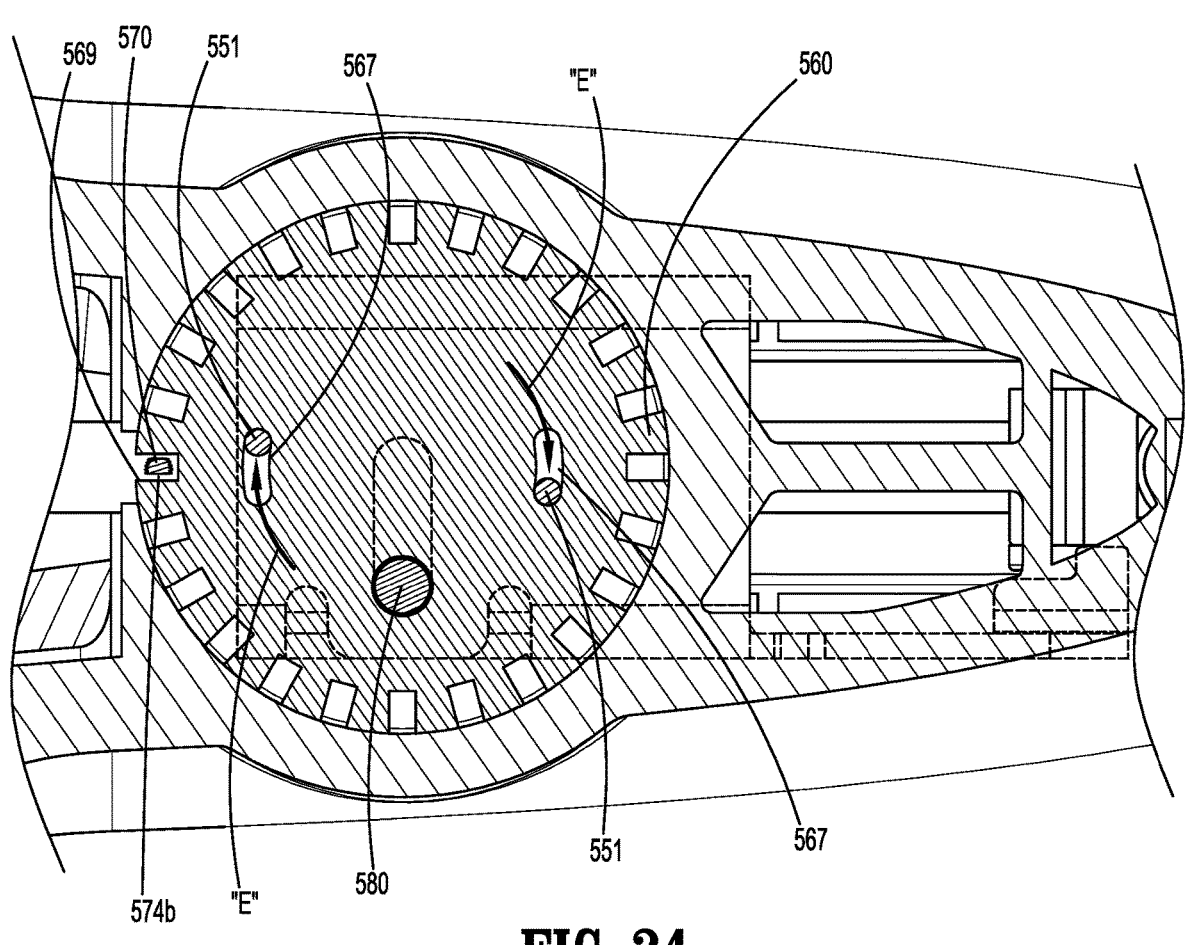
FIG. 24 is a cross-sectional view of the body of the rotation knob of FIG. 21 taken along section line 24-24 of FIG. 21.

FIG. 21-27 illustrate the use of the articulation assembly 500. The tool assembly 16 may be transitioned from the non-articulated configuration (FIG. 21) to the articulated configuration (FIG. 26) through rotation of the articulation knob 510. As the articulation knob 510 is rotated in the direction of an arrow "C" (FIG. 21), the drive bar 550 rotates with the articulation knob 510 as a single construct. Rotation of the drive bar 550 imparts rotation to the locking pin 570 such that the flat portion 574*b* and the tapered portion 574*c* of the locking pin 570 are rotated about 90 degrees in the direction of an arrow "D" (FIG. 23) or such that the flat and tapered portions 574*b*, 574*c* are radially aligned. During the rotation of the locking pin 570, the bosses 551 of the drive bar 550 are displaced within the slots 567 of the drive gear 560 in the directions of arrows "E" (FIG. 24). While the bosses 551 of the drive bar 550 are displaced towards one of the opposing ends of the respective slots 567 of the drive gear 560, the drive gear 560 is operatively disengaged from the drive bar 550. Under such a configuration, the drive gear 560 remains stationary during the rotation of the locking pin 570 of about 90 degrees as shown in FIG. 23.

Figure 25:
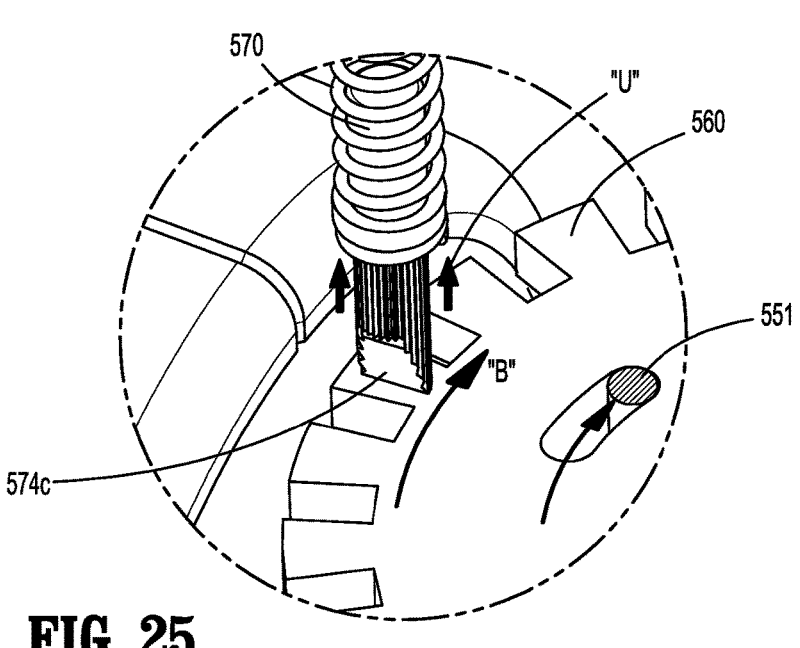
FIG. 25 is a partial perspective view of the articulation assembly of FIG. 24, illustrating operation of the locking pin.

Further rotation of the articulation lever 510 causes the bosses 551 to operatively engage the drive gear 560 to impart rotation to the drive gear 560. During the rotation of the drive gear 560 in the direction of arrow "B" (FIG. 25), the lateral wall 569 (FIG. 24) of the drive gear 560 engages the tapered portion 574*c* of the locking pin 570 and urges the locking pin 570 away from the drive gear 560 in the direction of arrows "U" (FIG. 25). As the drive gear 560 rotates, the drive pin 580 slides from one end of the slot 602 of the yoke 600 to an opposite end of the slot 602, which, in turn, causes axial displacement of the yoke 600 in the direction of an arrow "P" (FIG. 27). Such axial displacement of the yoke 600 imparts axial displacement to the articulation rod 650 (FIG. 11) and causes articulation of the tool assembly 16 as shown in FIG. 27.

Although the surgical device is illustrated as the stapling device 10, it is also envisioned that certain components described herein may be adapted for use in other types of articulating endoscopic surgical instruments including endoscopic forceps, graspers, dissectors, other types of surgical stapling instruments, powered vessel sealing devices and/or cutting devices. Further, although the stapling device 10 is illustrated as a manually actuated stapling device, it is envisioned that the aspects of this disclosure are also suitable for use with powered surgical stapling devices including robotically controlled stapling devices and electrically powered stapling devices. U.S. Pat. No. 9,055,943 ("the '943 Patent") discloses a surgical stapling device including an electrically powered handle assembly and U.S. Pat. No. 6,241,139 ("the '139 Patent") discloses a manually actuated handle assembly. For a more detailed description of construction and operation of an exemplary handle assembly and elongate body 14 which are suitable for use with the tool assembly 16 of the stapling device 10, see, e.g., the '943 and '139 Patents.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An articulation assembly for use with a surgical device comprising:
   a drive bar including a base and a stem extending therefrom, the base including first teeth;
   a locking pin engaging the first teeth of the drive bar;
   a drive gear operatively coupled to the drive bar, the drive gear including second teeth defining a gap between adjacent second teeth, the gap configured to receive a portion of the locking pin; and
   a yoke operatively coupled to the drive gear such that rotation of the drive gear causes axial displacement of the yoke, wherein rotation of the drive bar transitions the locking pin from a locked state to an unlocked state and rotates the drive gear when the locking pin is in the unlocked state such that the yoke is axially displaced.

2. The articulation assembly according to claim 1, wherein the drive gear defines a slot and the drive bar includes a boss slidable between opposing ends of the slot of the drive gear such that the drive bar imparts rotation to the drive gear when the boss engages one of the opposing ends of the slot of the drive gear.

3. The articulation assembly according to claim 1, wherein the locking pin includes a spring biasing the locking pin towards the drive gear.

4. The articulation assembly according to claim 1, wherein the locking pin includes a tapered portion configured to engage a lateral wall of the second teeth of the drive gear, the lateral wall defining a portion of the gap such that the tapered portion of the locking pin enables the locking pin to slide over the lateral wall of the second teeth to enable rotation of the drive gear.

5. The articulation assembly according to claim 1, further comprising a knob coupled to the stem of the drive bar for concomitant rotation therewith.

6. The articulation assembly according to claim 5, further comprising a cover defining a bore to receive the stem of the drive bar therethrough, the cover including a stopper to limit rotation of the knob by a predetermined amount.

7. The articulation assembly according to claim 1, further comprising a drive pin coupling the drive gear to the yoke.

8. The articulation assembly according to claim 7, wherein the drive pin is coupled to the drive gear off-center.

9. The articulation assembly according to claim 7, wherein the yoke defines a slot configured to receive the drive pin.

10. The articulation assembly according to claim 9, wherein the slot of the yoke is orthogonal to a longitudinal axis defined by the yoke.

11. The articulation assembly according to claim 1, wherein the drive bar defines a slot dimensioned to receive the locking pin therethrough.

12. The articulation assembly according to claim 11, wherein the drive bar includes an inner surface that defines a portion of the slot of the drive bar and has the first teeth.

13. The articulation assembly according to claim 12, wherein the slot of the drive bar has a semi-circular profile.

14. A surgical instrument comprising:

an elongate body including proximal and distal portions;

an articulation assembly including:

a drive bar including a base and a stem extending from the base;

a locking pin rotatably coupled to the base of the drive bar;

a drive gear operatively coupled to the drive bar, the drive gear including teeth defining a gap between adjacent teeth, the gap configured to receive a portion of the locking pin; and a yoke operatively coupled to the drive gear such that rotation of the drive gear causes axial displacement of the yoke;

a tool assembly supported on the distal portion of the elongate body; and an articulation rod interconnecting the yoke and the tool assembly such that axial displacement of the yoke causes articulation of the tool assembly, wherein rotation of the drive bar transitions the locking pin from a locked state to an unlocked state and rotates the drive gear when the locking pin is in the unlocked state such that the yoke is axially displaced to articulate the tool assembly.

15. The surgical instrument according to claim 14, wherein the drive gear has a slot and the drive bar includes a boss slidable between opposing ends of the slot of the drive gear such that the drive bar imparts rotation to the drive gear when the boss engages one of the opposing ends of the slot of the drive gear.

16. The surgical instrument according to claim 14, wherein the drive bar defines a slot and includes a side wall defining a portion of the slot of the drive bar, the side wall including teeth configured to engage the locking pin.

17. The surgical instrument according to claim 16, wherein the locking pin includes a spring biasing the locking pin towards the drive gear.

18. The surgical instrument according to claim 16, wherein the locking pin includes a tapered portion configured to engage a lateral wall of the teeth of the drive gear defining a portion of the gap such that the tapered portion enables the locking pin to slide over the lateral wall of the teeth of the drive gear to enable rotation of the drive gear.

19. The surgical instrument according to claim 15, wherein the articulation assembly further includes a pad interposed between the drive bar and the drive gear, the pad having an annular configuration.

20. The surgical instrument according to claim 15, wherein the articulation assembly further includes a knob coupled to the stem of the drive bar for concomitant rotation therewith.

\* \* \* \* \*